United States Patent [19]

Jacobs et al.

[11] Patent Number: 5,620,860
[45] Date of Patent: Apr. 15, 1997

[54] METHOD FOR WASHING IMMUNOASSAY ELEMENTS

[75] Inventors: Merrit N. Jacobs, Fairport, N.Y.; Russel H. Marvin, Riverton, Wyo.; Douglas J. Dychko, Rochester, N.Y.

[73] Assignee: Johnson & Johnson Clinical Diagnostics, Rochester, N.Y.

[21] Appl. No.: 393,632

[22] Filed: Feb. 24, 1995

[51] Int. Cl.$^6$ .................................................. G01N 33/53
[52] U.S. Cl. ...................... 435/7.9; 422/56; 435/7.91; 435/7.92; 435/7.93; 435/7.94; 435/7.95; 435/962; 435/968; 435/969; 435/970; 436/538; 436/539; 436/540; 436/541; 436/542; 436/546; 436/825
[58] Field of Search ............................ 422/56; 435/7.1, 435/7.9–7.95, 962, 968–970; 436/538–542, 546, 825

[56] References Cited

U.S. PATENT DOCUMENTS

| | | | |
|---|---|---|---|
| 4,517,288 | 5/1985 | Giegel et al. | 435/7 |
| 4,670,381 | 6/1987 | Frickey et al. | 435/7.93 |
| 4,752,562 | 6/1988 | Sheiman et al. | 435/5 |
| 4,774,174 | 9/1988 | Giegel et al. | 435/5 |
| 4,786,606 | 11/1988 | Giegel et al. | 435/500 |
| 4,857,471 | 8/1989 | Salzman et al. | 436/43 |
| 5,155,024 | 10/1992 | Erkenberry | 435/7.9 |
| 5,232,663 | 8/1993 | Wilk et al. | 422/56 |
| 5,372,932 | 12/1994 | Friedman et al. | 435/7.9 |

*Primary Examiner*—Carol A. Spiegel
*Attorney, Agent, or Firm*—Dana M. Schmidt

[57] ABSTRACT

A method of dispensing wash solution to separate free from bound labels in a slide immunorate assay. The method comprises dispensing wash first as separate drops spaced to allow complete absorption prior to the next drop, followed by a time at which the rate of dispensed wash exceeds the rate of fluid uptake of the slide, to form a continuous stream. The first phase of this wash method provides a more complete separation of bound from free under the dispense tip than occurs if only a continuous stream is used throughout.

8 Claims, 7 Drawing Sheets

FIG. 1

FIG. 2A TIME (INITIAL RATE)

FIG. 2B TIME

METHOD FOR WASHING IMMUNOASSAY ELEMENTS

FIELD OF THE INVENTION

This invention relates to a method of dispensing wash solution onto immunorate slide test elements to achieve improved separation of free labels from bound labels.

BACKGROUND OF THE INVENTION

It is well-known in the field of immunoassays using dried test elements, that free, uncomplexed labels need to be separated and removed from bound or complexed labels, prior to detection. This is done by applying, after the sample is added, a wash liquid to the test element after the complexing reaction has occurred, to cause chromatographic separation of the free labels from those that are bound. Such separation, in theory, leaves a volume in the test element in which the bound labels can be read free of the interference of the uncomplexed ones that are now washed away. The process is exemplified by the following U.S. Pat. Nos. 4,517,288; 4,752,562; 4,774,174 and 4,786,606. It is well understood that the label can be attached to a immunoreactant for competitive assays, or to an antibody for sandwich assays, either process being of use in this invention.

In practice, however, notwithstanding at least 9 years of existence of such patents, such a process does not always work well. The practice taught by said patents has been to apply a static "stream of (eluting) solvent" to the center of the reaction zone. That is, a dispensing tip is positioned above a test element already wetted with patient sample, above the substantial center of the reaction zone, and a stream continuously pours out onto that center of the reaction zone. The tip stays fixed relative to the test element during washing. It turns out that such a continuous flow produces underneath the center thereof, in certain test elements, a portion in which the free labeled immunoreactant do not get washed out.

The causal mechanism for this artifact was not understood prior to this invention. The artifact meant that reading could not be centered on the spot that was washed, without being affected by this artifact. Indeed, an unwashed center of the wash zone drastically reduces the useful read portion, as will be readily understood.

Still another problem with the conventional stream method of washing has been that unacceptable background rates and/or biases have been detected with certain chemistries. The causal mechanisms for these biases following washing, have also been unknown. The problem of background and biases has been particularly troublesome in immunoassays that are rate assays.

Hence, prior to this invention there has been a long-felt need for a wash protocol that effectively removes the unbound labeled immunoreactants from substantially all of the washed volume, including that centered on the wash liquid that impacts the test element. There has been a further need to eliminate the background "noise" and biases that sometimes occur.

(As used herein, "labeled immunoreactant" means any labeled antibody or antigen that is used to detect a target analyte, such as an antigen or antibody, whether the assay be via a competitive assay in which a target antigen, for example, competes with a labeled version of the antigen, or a sandwich assay in which a target antigen, for example, forms a sandwich between a capture antibody and a labeled antibody (the labeled immunoreactant). The label in turn can be any useful detectable direct or indirect indicator, e.g., a fluorophor or an enzyme, respectively.)

SUMMARY OF THE INVENTION

We have developed a method of washing test elements for immunoassays that solves the above-noted problems. It is based on the discovery that dropwise dispensing at a rate less than the fluid uptake rate of the slide test element, causes successive drops to wash through the heretofor unwashed center of the element portion covered by any lens left on the surface.

More specifically, in accord with one aspect of the invention there is provided a method of separating bound labels from free labels in an immunoassay conducted on a test element containing dried reagents prior to contact with a sample liquid, the method comprising the step of depositing a wash liquid onto a portion of the test element containing both bound and free labels so that the deposited wash liquid can remove at least some of the free labels. The method is improved in that the depositing step comprises the steps of a) initially depositing the wash liquid a drop at a time at a rate that is less than the rate of uptake of each drop by the portion of the test element, so that a minimal residual meniscus of wash liquid remains at the surface of the portion when the next drop of wash liquid is applied;

and b), after a plural number of drops are applied as per step a), applying the wash liquid at a rate that exceeds the rate of uptake of liquid as it currently exists in the test element portion being contacted by wash liquid in step b), and more than a minimum residual meniscus does remain on the surface when the next drop of wash liquid is applied, so that during step b) only, a lens of wash liquid forms and remains during washing on the surface, to extend the area of effective wash.

In accord with another aspect of the invention there is provided a method of separating bound labels from free labels in an immunoassay conducted on a test element containing dried reagents prior to contact with a sample liquid, the method comprising the step of depositing a wash liquid onto a portion of the test element containing both bound and free labels so that the deposited wash liquid can remove at least some of the free labels. The method is improved in that the depositing step comprises the steps of depositing at least some of the wash liquid on each test element within about 30 sec, a separated drop at a time, each drop having a volume no greater than about 3 μL, so that adequate washing occurs directly underneath the drop deposition.

In accord with yet another aspect of the invention, there is provided a method for separating bound labels from free labels is improved in that the depositing step comprises the steps of a) repeatedly washing the portion of a test at the approximate center of the contact of deposited wash liquid by repeatedly passing a contact meniscus of deposited liquid through the portion, and b) thereafter expanding the contact meniscus out beyond said portion of the test element to be washed.

Accordingly, it is an advantageous feature of the invention that a substantial improvement in background noise is achieved in washed immunoassays.

It is a related advantageous feature of the invention that the signal-to-noise ratio is improved by at least 50% for at least phenobarbital assays.

Yet another related advantageous feature is that a substantial reduction in certain biases is achieved for such immunoassays.

Another related advantageous feature of the wash method of the invention is that it allows for detection in so-called dried test elements, of immunoassay rates that would be difficult to achieve using conventional wash methods, due to the signal being swamped by the background noise.

A further advantageous feature of the invention is that it produces better uniformity of results in the area washed by the wash liquid.

Yet another advantageous feature is that the invention reduces the Z-axis sensitivity of the slide test elements (sensitivity to variations caused solely by differences in vertical distance between the slide element and dispensing tip during liquid dispensing).

Other advantageous features will become apparent upon reference to the Detailed Description that follows, when read in light of the attached drawings.

DESCRIPTION OF THE PREFERRED EMBODIMENTS

The following description is presented in the context of preferred embodiments, in which the test element is a certain kind of immunoassay, e.g. phenytoin or phenobarbital, in a particular test element format that uses an enzyme and substrate for a rate detection of the bound labels or labeled antibodies; and a particular wash solution applied away from the center of the reaction zone of the element. Thus, the rate of color development by the substrate is detected. In addition, the invention is useful regardless of a) which analyte is being immunoassayed, b) which dried test element format is used, c) which detection chemistry among the many well-known chemistries, is used, d) whether the detection is of a rate or an end-point, e) what the wash solution comprises, and f) where on the test element the wash is applied. The reason is that the invention goes to the heart of the flow mechanisms that occur when any so-called dried test element previously spotted with a sample, is attempted to be washed, and makes use of those flow mechanisms.

Thus, a preferred test element to which the wash process of this invention is applied is the following phenobarbital test element.

All washing experiments hereinafter described, were performed on assay elements for phenobarbital (a preferred test element for use with this invention) having the following format and composition:

| Phenobarbital Assay Element | | |
|---|---|---|
| Layer | Components | Dry Coverage (g/m²) |
| Gravure | 3',5'-Dichloro-4'-hydroxyacetanilide | 0.00995 |
| | 4,5-Dihydroxy-3-(6,8-disulfo-2-naphthylazo)-2,7-naphthalenedisulfonic acid, sodium salt | 0.0538 |
| | 3-(N-morpholino)propanesulfonic acid | 0.0450 |
| | Bovine serum albumin | 0.00022 |
| | Polyacrylamide | 0.00108 |
| | Triton ™ X-100 Surfactant (Union Carbide) | 0.00430 |
| * | Phenobarbital-horseradish peroxidase conjugate | 0.00001 |
| ** | Modified apo-horseradish peroxidase | 0.01 |
| Spreading Layer | N-[tris(hydroxymethyl)methyl]-2-aminoethanesulfonic acid | 0.219 |
| | Dimedone | 0.50 |
| | 3',5'-Dichloro-4'-hydroxyacetanilide | 0.22 |
| | Vanadyl sulfate | 0.040 |
| | Mannitol | 1.0 |
| | Glycerol | 2.0 |
| | Bovine serum albumin | 1.0 |
| | 4,5-Bis(4-dimethylaminophenyl-2-(3,5-dimethoxy-4-hydroxyphenyl)imidazole | 0.20 |
| | Tetronic ™ T908 surfactant (BASF Corp.) | 0.02 |
| | Surfactant 10G ™ surfactant (Olin Chem. Co. | 0.248 |
| | Poly(methyl acrylate-co-sodium 2-acrylamido-2-methylpropanesulfonate-co-2-acetoacetoxyethyl methacrylate) | 2.583 |
| | Poly(vinyltoluene-co-methacrylic acid) (~30 μm beads) | 130.0 |
| *** | Polymer particle-antibody conjugate | 0.15 |
| Gel Layer | Gelatin | 10.0 |
| | 3',5'-Dichloro-4'-hydroxyacetanilide | 0.44 |
| | N-[tris(hydroxymethyl)methyl]-2-aminoethanesulfonic acid | 4.58 |
| | Triton ™ x-100 surfactant (Union Carbide) | 0.02 |
| | Bis(vinylsulfonylmethyl) ether | 0.150 |
| | Poly(ethylene terephthalate) support | |

*The phenobarbital-horseradish peroxidase conjugate employed is that of Example 6 of U.S. Pat. No. 5,298,403 issued March 29, 1994.
**The modified apo-horseradish peroxidase employed is that of Preparation 2 of U.S. Ser. No. 277,391 of R. E. Shoke filed July 19, 1994.
***The polymer particle-antibody conjugate employed is poly[styrene-co-3-)p-vinylbenzylthio)propionic acid] (weight ratio 95/5) having an antibody to phenobarbital covalently bound thereto.

The basic immunoassay process for such a test element is well understood, so that the following summary suffices: A patient sample (e.g., serum or urine) is deposited onto the test element, a short incubation follows, a portion of the element so deposited with sample is washed, and further incubation follows. Thereafter, a portion of the washed portion is read several times with a densitometer to determine the rate of color development, and this rate is compared to calibrated results that are predictive of the concentration of the analyte—in this case, phenobarbital.

Figure 1:
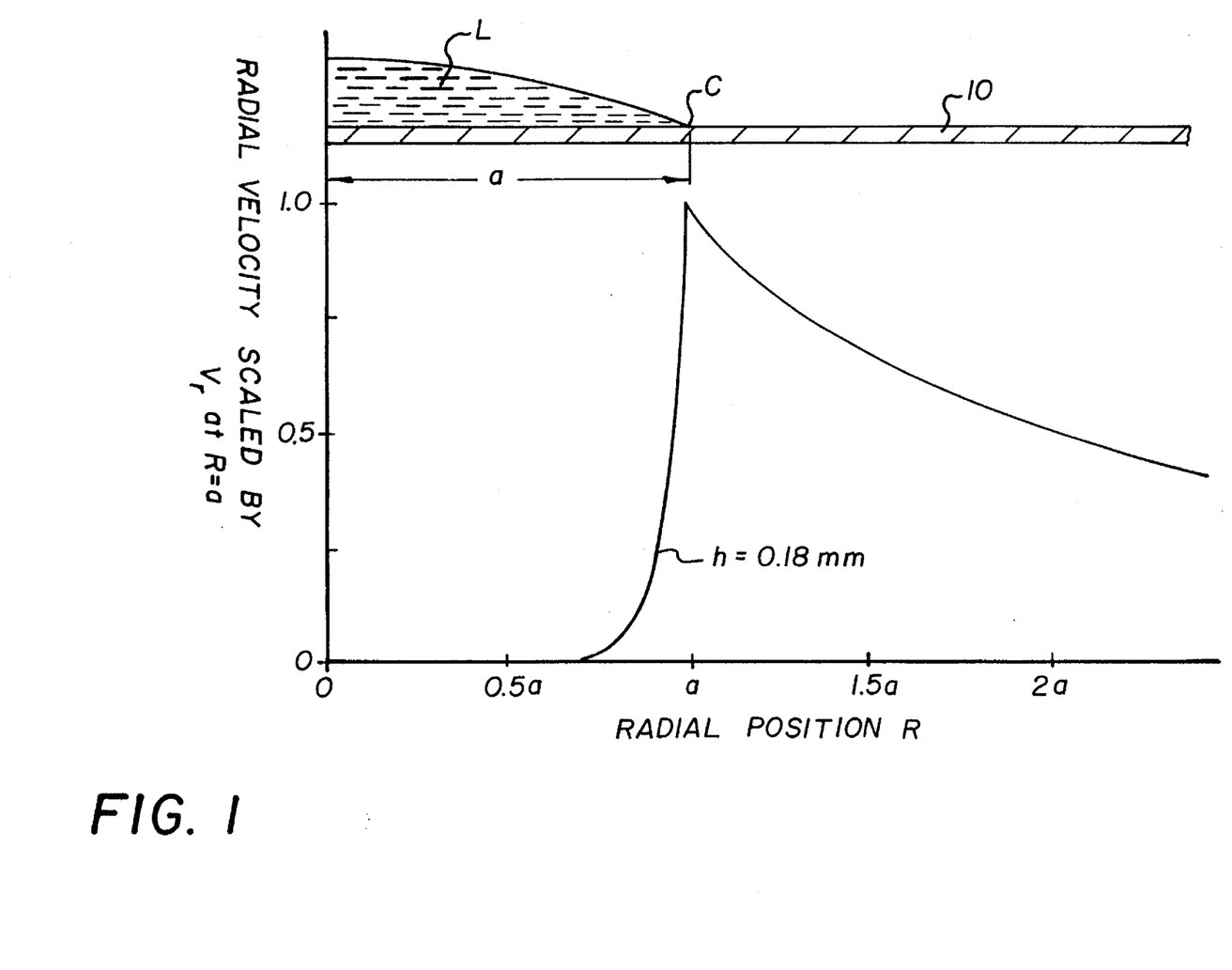
FIG. 1 is a plot of flow velocities within a test element as a function of distance from the contact meniscus.

FIG. 1 explains what is currently believed to be the underlying mechanism of the invention, that is, the nature of liquid flow within a thin slide test element of the kind herein described. That is, it can be shown that for a liquid lens L having a contact meniscus C sitting on a thin slide test element 10 of the type described herein, the velocity of flow into and within that element 10 is a function of the horizontal distance from the edge of the contact meniscus C to the portion of the test element whose velocity of flow is being measured. Thus the maximum flow into and through element 10 occurs at a radial positon, shown arbitrarily as velocity= 1. For radial position R<<a, the velocity falls off rapidly to essentially zero. As R is increased beyond "a", the flow velocity also decreases, but not as rapidly.

Most of the background noise and biases caused by total protein heretofore encountered, and now solved by this invention, can be understood from the aforedescribed mechanism. "Dried" test elements 10, FIG. 2A, already bearing the patient sample, have certain internal flow characteristics when washed, that heretofore have not been publicly known. (Element 10 has an exposed upper surface 11.) As shown, FIGS. 2A and 2B, element 10 is maintained stationary with respect to dispense tip 12. However, the invention herein described is just as useful if relative horizontal motion is provided between the two to create a moving wash, as described and claimed in related U.S. Ser. No. 08/470,100, filed on Jun. 6, 1995, entitled "Washing A Slide At Different Locations.

Figure 2A:
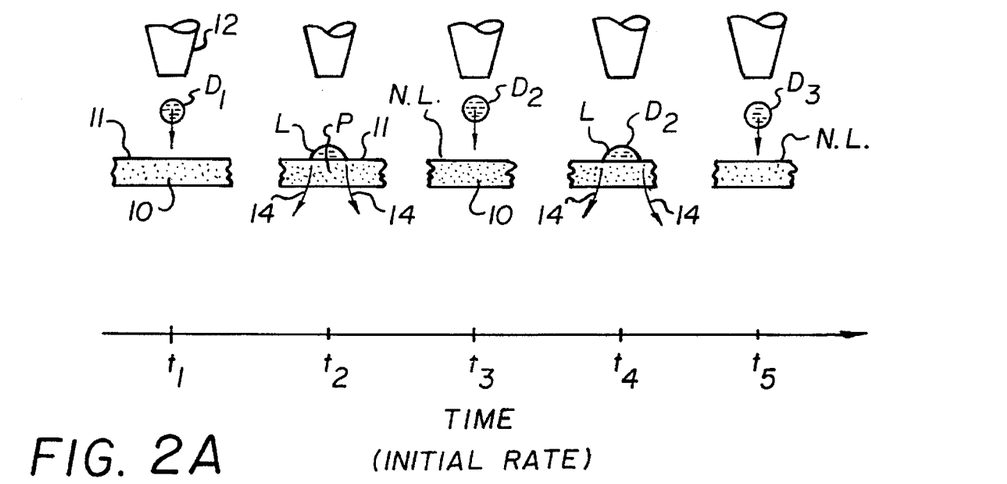
FIGS. 2A and 2B are partially schematic depictions over time of the process of the invention starting from the very first washing, $t_1$, to the end of the washing, $t_{i+5}$.

In the invention, a disposable tip 12 is programmed to dispense drops of wash onto surface 11 of element 10, initially at a rate that is slower than the uptake rate of element 10. The height of the tip 12 above the surface 11 is maintained at a distance appropriate to the size of drops desired. For example, a height of 2.54 mm is preferred for 0.5 microliters of drop volume.

At time $t_1$, the first drop $D_1$ is dispensed and is shown as "falling" onto the element 10. (Separation need not be such as to produce an actual free-falling drop. The separation and free-fall is shown only to aid in visualization.) Shortly thereafter, at time $t_2$, the drop is on the test element, with a portion of the drop diffusing generally downwardly, arrows 14, before diffusing outwardly, with a meniscus still protruding to form a lens L above the surface 11 of element 10. It is crucial to note that arrows 14 for the wash vector are located mostly at the edge of lens L—very little washing occurs inside of the lens or inside of arrows 14 at center point P. Hence, drops $D_1$ through $D_i$ are preferably of reduced volume (discussed below.)

Before the next drop $D_2$ is released at time $t_3$, most and preferably all, of the lens L of drop $D_1$ is completely absorbed—this is the meaning of a wash dispense rate that is less than the fluid uptake rate of the test element at this time. The complete absorption of $D_1$ is symbolized by the label "N.L." for "no lens". The fluid conditions for drop $D_2$ at time $t_4$ are of course substantially the same as shown for drop $D_1$ at time $t_2$.

Figure 4:
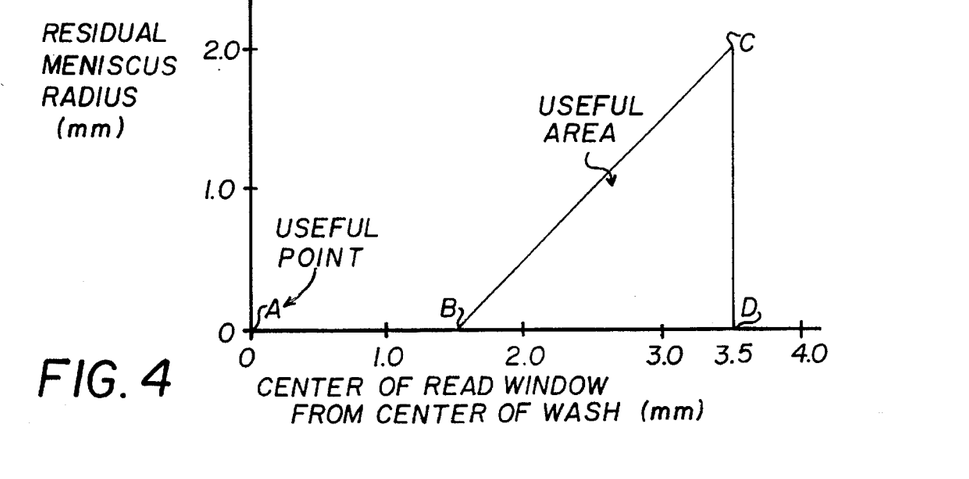
FIG. 4 is a discontinuous plot of the read distance off-center versus useful residual meniscus radii for a preferred slide test element format, which illustrates both the useful zero, zero condition and the values useful if the residual meniscus radius is greater than zero.

Although the most preferred condition of complete absorption is shown in FIG. 2A, the invention also contemplates the absorption between drops of all but a minimal remaining meniscus. As used in this invention "minimal remaining meniscus," means, for a read window radius of 1.5 mm and a cover sheet optical window radius of 5 mm, the minimal remaining meniscus just prior to the addition of the next drop, any amount just short of that which will overlap the read window, because the area under the minimal remaining meniscus may not be properly washed. This is defined graphically, FIG. 4, to be point A at 0,0 values and the inclusive area of triangle ABC. (Differing values will occur for a slide of different construction.) That is, as will be readily understood, a read window radius of 1.5 mm limits the distance of the center of the read window from the center of the wash to be, between 1.5 and 3.5 mm if the maximum optical window radius is 5.0 mm. Because any non-zero radius of the minimal remaining meniscus creates a non-washed area thereunder, as described herein, any non-zero minimal remaining meniscus must force the read distance off the center of the wash a distance of $\leq 1.5$ mm, which linearly increases thereafter. A zero radius will allow, however, a zero read distance off-center (point A). A primary benefit of the invention is that now, point A is useful for the first time, because the volume under point A is properly washed.

Figure 3:
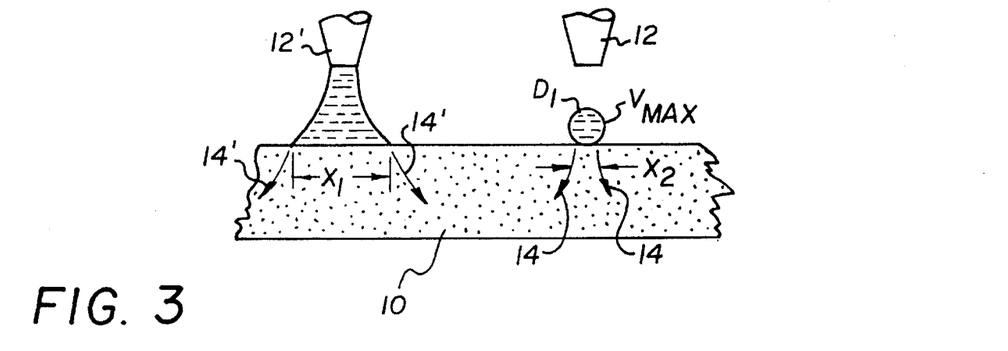
FIG. 3 is a depiction similar to that of FIG. 2A, comparing the size of the impact area caused by separated drops to that for a conventional continuous stream.

The above described initial rate at less than the fluid uptake rate of the test element provides for a prescribed number of drops "i", which can vary, depending on a number of factors, not the least of which is the drop size, discussed in more detail hereinafter regarding FIG. 3. A useful example of the number of repeats "i" is 5 such drops. Because of the need to limit the total wash dispense time to a short duration, e.g., no more than about 60 sec., the maximum time for the dispensing of wash in separate drop format is about 30 sec. Most preferably, it is much less than that, e.g., no more than 18 sec.

Figure 2B:
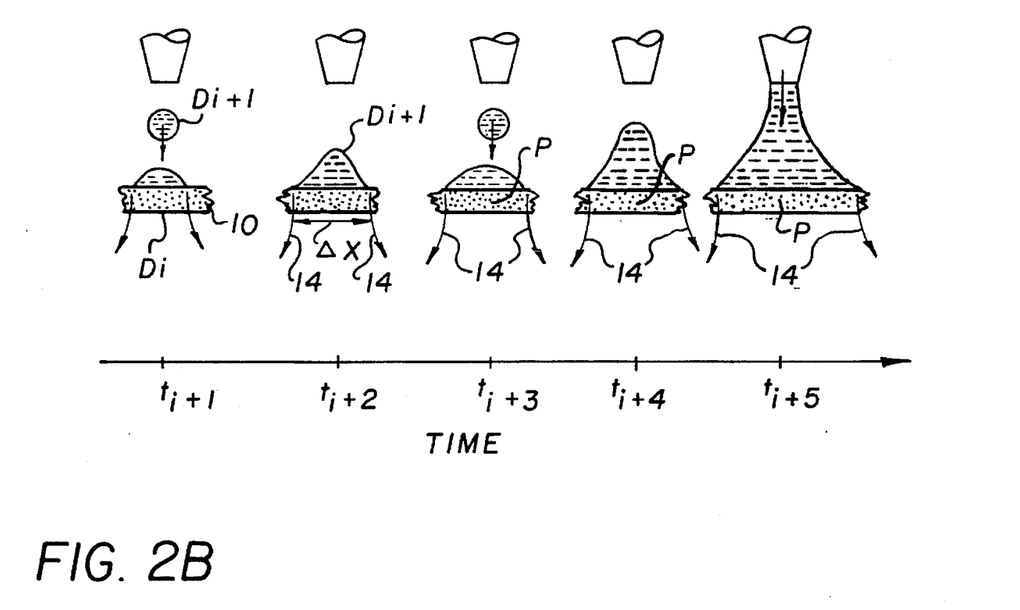

The next phase of the invention, FIG. 2B, preferably is that in which the rate of dispense of wash exceeds the current uptake rate of the test element—either by an absolute increase in the dispense rate or by reason of the fact that the uptake rate of the test element has declined due to the increased amounts of fluid already present.

Thus, at time $t_{i+1}$ (where $t_i$ is the total time to produce i drops in the process of FIG. 2A), a drop $D_{i+1}$ is being deposited, FIG. 2B, while the lens from drop $D_i$ is still present. The effect is, to increase the size of the contact meniscus or lens L of drop $D_{i+1}$ at time $t_{i+2}$. Importantly, this spreads apart the wash diffusion vectors 14 a distance $\Delta x$ so that they become farther and farther apart, through time $t_{i+5}$, as the lens enlarges upon element 10. For this reason, all washing occurs farther and farther from the center point P, FIG. 2A. This constitutes an expansion of the diameter of the contact meniscus out to the boundary of the washed portion, at time $t_{i+5}$. Inasmuch as the dispense rate now exceeds the uptake rate of element 10, the liquid buildup on surface 11 is such that, by time $t_{i+5}$, the dispensing becomes a continuous stream rather than individual drops.

It will now be seen that the problem with conventional washes has been that they fail to provide the steps of FIG. 2A, hence providing insufficient washing in the region of center point P. The current method however minimizes that.

As noted, the volume of drops $D_1$ through $D_i$ for "i" drops is a preferred factor. Drops that are preferred are those that produce initial contact diameters that are as small as possible, and at least smaller than the diameter of a continuous stream. The reason for the preference for small volumes is the limited capacity of the slide test element and hence of the volume of wash to be supplied. E.g., "i" drops at 3 µL using a total volume of 12 µL allows only 4 drops in total, a marginal value of "i", given that some of the drops need to expand the lens diameter. In FIG. 3, tip 12', on the left, is a conventional tip dispensing a continuous wash stream, producing a lens on element 10 that has a maximum diameter of contact $X_1$ that is about 1 mm. This in turn produces the wash vectors 14' that are spread "too far apart" as described in FIG. 2B (which is acceptable if limited to only stages such as $t_{i+4}$ and $t_{i+5}$. Vectors 19', FIG. 3, leave unwashed a large portion of element 10 directly underneath tip 12'. However, when dispensing at a rate less than the uptake rate, a drop $D_1$ whose volume $V_{max}$ does not exceed about 2 microliters, as shown on the right, there is produced a contact lens by drop $D_1$ that has a maximum diameter $X_2$ that is much less than $X_1$. Hence, wash vectors 14 are much closer together and they leave very little unwashed portion of element 10 under tip 12. Volumes larger than 3 µL are disadvantageous for 2 reasons—they produce a total wash volume, once the stream condition of FIG. 2B occurs, that is too large, and they produce a contact diameter $X_2$ that is not much less than $X_1$. Hence, drop volumes no larger than 2 µL are most preferred.

Because the total wash volume should not exceed about 14 µL, using a value of "i"=5 drops, this means that $V_{max}$ for each of drops $D_1$ through $D_5$ is most preferably from 0.5 to about 1 microliter.

Although, as described, the preferred procedure incorporates the step sequence of FIG. 2B to produce a continuous stream, it is yet another alternative to dispense all of the wash liquid in the drop forms as described in FIG. 2A only, wherein absorption takes place between drop dispensing to leave only a minimum residual meniscus on the surface of the test element. The reason why the addition of the sequence of FIG. 2B is preferred over following just FIG. 2A, is that FIG. 2B acts to push the washed free labels farther out and speeds up the time of wash.

As noted at the beginning of this discussion, the wash dispensing of the invention can take place at any portion of the reaction zone, including the center, in which the patient sample reacts with the contents of element 10. Most preferably, the reading step occurring after further incubation is centered on the center of the wash step, again wherever that happens to be.

Figure 5:
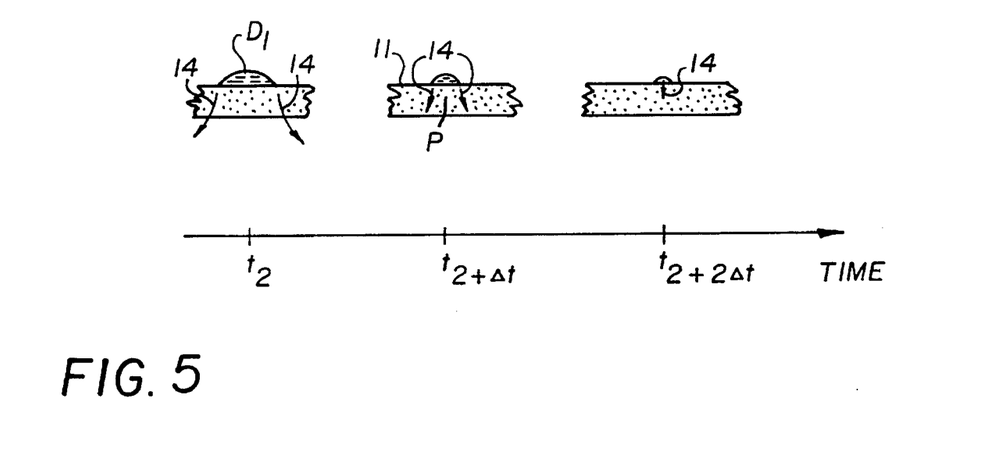
FIG. 5 is a depiction similar to that of FIG. 2A except that it is an "enlargement" of the events occurring between time $t_2$ and time $t_3$.

FIG. 5 illustrates that the invention is useful even if $X_2$ is not that much smaller than $X_1$. The fact the drop is allowed to be fully absorbed before the next drop strikes, allows even the volume between vectors 14 of FIG. 3, to be washed. Thus, the events at time $t_2$ are identical to those of $t_2$ of FIG. 2A. However, at time $T_{2+\Delta_t}$, drop $D_1$ is further absorbed, thus shrinking the lens to a diameter smaller than $X_2$, bringing the wash vectors 14 closer together. As the drop vanishes from surface 11, at time $t_{2+2\Delta_t}$, vectors 14 come together (albeit with much reduced magnitude), helping to wash any center portion P heretofore unwashed. In this fashion, the invention repeatedly washes the approximate center portion (P) of the test element that is directly underneath the dispensing tip (shown in FIG. 3), prior to expanding the contact meniscus, FIG. 2B, out to the boundary of the washed portion of the element. In contrast, a flow of liquid in steady-stream form fails to provide the lens-vanishing phenomenom of FIG. 5 and hence fails to wash portion P.

There are several ways in which the dispense rate can exceed the uptake rate of element 10 as shown in FIG. 2B. One is to provide an absolute increase in the dispense rate so that the rate occurring as shown in FIG. 2B exceeds the rate occurring as shown in FIG. 2A. The simplest, however, is to keep the dispense rate constant, at a value however which ends up crossing over the fluid uptake rate of element 10 as the latter declines due to the ever-increasing amounts of liquid already present.

Figure 6:
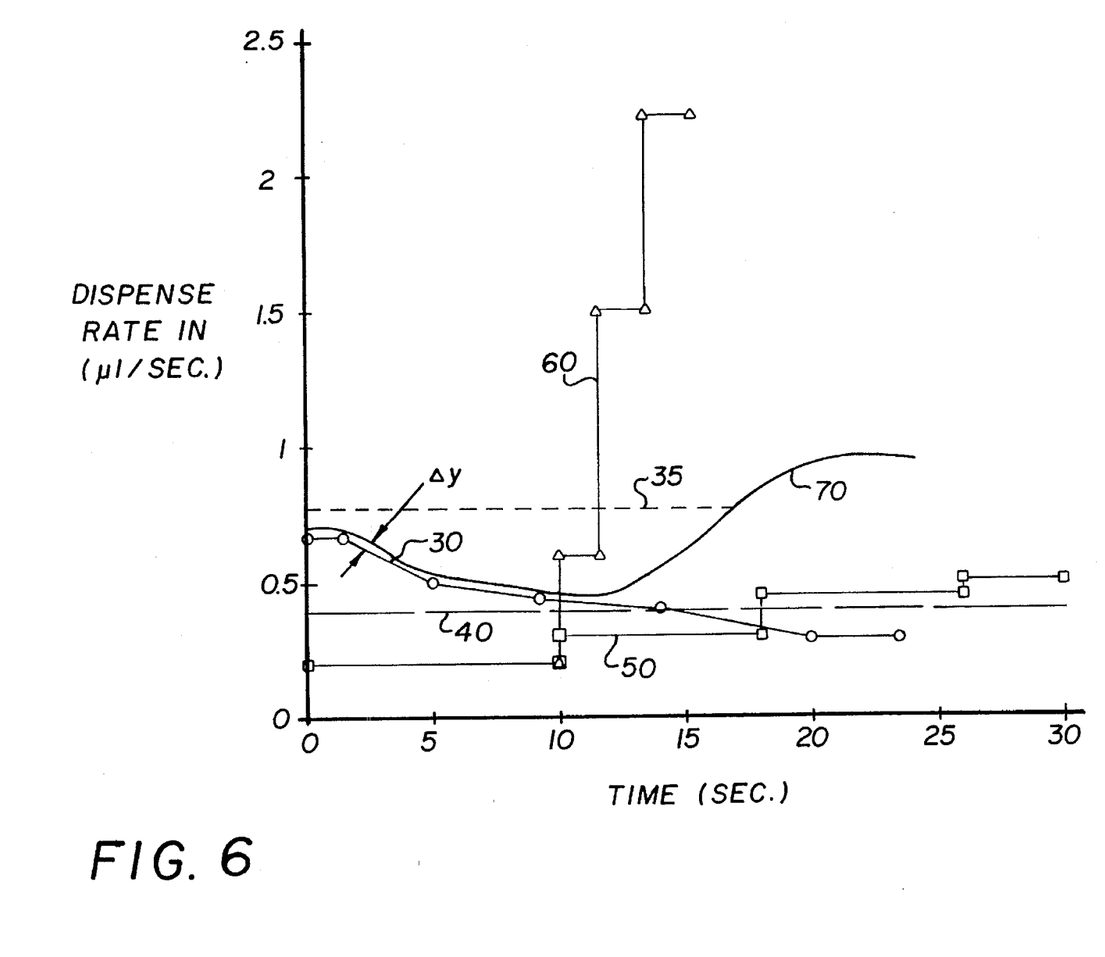
FIG. 6 is a plot of the uptake rate of a test element used with the invention, compared to the wash dispense rate of the invention.

Both of these options are illustrated in FIG. 6. Curve 30 is the rate of fluid uptake that occurs in the phenobarbital element described above, over a time period of from 0 to 25 sec. Curve 30 was produced by dispensing the above wash solution to the surface of a phenobarbital test element described above, while controlling and recording the dispensing rate so as to maintain a 1 mm diameter lens over the dispensing event. The fact that the lens diameter neither increased nor decreased as dispensing occurred meant that the rate of dispense so used was in fact the same rate of fluid uptake of the test element.

Rate values exceeding curve 30 will flood the test element beyond its uptake capability. For example, straight-line curve 35 is the approximate dispense rate for washes of immunoassays conventionally available on the analyzer available under the trademark "E250"® from the Clinical Diagnostic Division, formerly of Eastman Kodak Company. As is apparent, the dispense rate of curve 35 creates surface fluid.

In accordance with the invention, the initial dispense rate to produce the condition of FIG. 2A, starts at a rate below curve 30, FIG. 6, e.g., at the rate of 0.4 µL/sec (straight line 40) or 0.2 µL/sec (curve 50). In either case, the uptake rate of the slide exceeds the dispense rate so that the residual meniscus radius of lens L, FIG. 2A, goes to zero until curves 40 or 50 cross over curve 30. At that point, the conditions of FIG. 2B start and the wash becomes a continuous stream.

Still another useful curve, FIG. 6, is curve 60. This last alternative is more advantageous in that the entire wash sequence is completed the fastest, within about 15 sec. In all cases, however, the period of time when the wash dispense is in the form of individual drops, FIG. 2A, is less than 20 sec.

Not shown in FIG. 2A, but useful nonetheless, is initial dispense rates that cause a non-zero residual meniscus radius to be left between drops. Such a rate, for example, could be that which forms curve 70, FIG. 6. The amount of separation Δy will of course depend upon where in the area of triangle ABC, FIG. 4, the invention is being practiced for a slide test element constructed as described.

EXAMPLES

The following examples illustrate a preferred use of the invention and the benefits achieved therefrom. The slide test elements used were the phenobarbital elements described above. For the "patient sample," a solution of 30 mg/dL of phenobarbital and 10 g/dL of total protein, identified as TP10, was used. The test was conducted an analyzer equivalent to the "E250"® Analyzer available from Clinical Diagnostic Systems, Inc., formerly of Eastman Kodak Company, by the steps of:

1) Spotting 11 µL of the above test sample on each slide,
2) Incubating 5 minutes at 37° C.,
3) Washing using the protocols described below, and
4) Determining the dye formation rate by reading the reflection densities (Dr) over a 2.5 minute read time at 680 nm while incubating at 37° C. and converting the Dr values to (Dt) by the conventional Clapper-Williams transform. The rates were calculated by subtracting transform densities between sequential pixels between 33 and 40 sec after the beginning of wash.

The wash solution employed in the experiments, and useful with the invention, had the composition:

| | |
|---|---|
| Hydrogen peroxide | 0.03% |
| Sodium Phosphate (pH 6.8) | 10 mM |
| 4'-Hydroxyacetanilide | 5 mM |
| Diethylenetriaminepentaacetic acid | 10 mM |
| Hexadecylpyridinium chloride | 0.1% |

Example 1

Conventional Wash Using a Stream (Comparison Example)

Figure 7A:
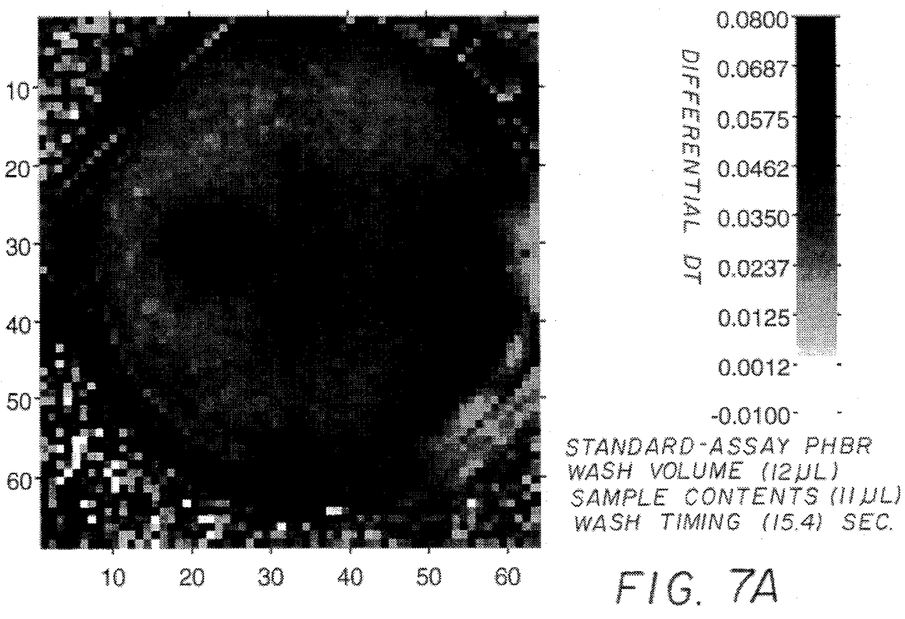
FIGS. 7A and 7B are each a computer mapping, using 4×4 grouped pixels, of the differential densities produced by a conventional wash and the wash of the invention, respectively, detected at those grouped pixels over a fixed period of time, so as to depict a rate of change of density at each grouped pixel location, the darker gray being indicative, as noted by the associated gray scale color map, with a rate of change that is greater than the lighter grays.

In this example, the wash was supplied as a steady stream at a fixed rate of 10 μL over 15.4 sec, at a location that was 3.2 mm left of the center of the slide. The rate (not the raw density) produced as a result is depicted in FIG. 7A over the entire optical read window. (The mapping was achieved for 4×4 pixels graphed as a group of 16 to form one "location," wherein the reflection density determined as noted above, at 2 different, fixed times, was subtracted one from the other). As shown by the map of FIG. 7A, a much higher rate of change appeared at the location of the dispersed wash solution, namely at the dark spot to the left of center. This spot represents unwashed free label, which as explained above, occurs because the conventional practice of dispensing the wash as a stream is unable to wash completely the portion of the test element that is directly below the dispenser tip.

FIG. 7A's image also includes the approximate area of actual read. The diameter of such a circle is approximately 3 mm. If, as is shown in FIG. 8, that window is slightly displaced off the center of the element, there is a substantial chance it will pick up a portion of the aforesaid dark spot, creating a bias in the read.

Figure 8:
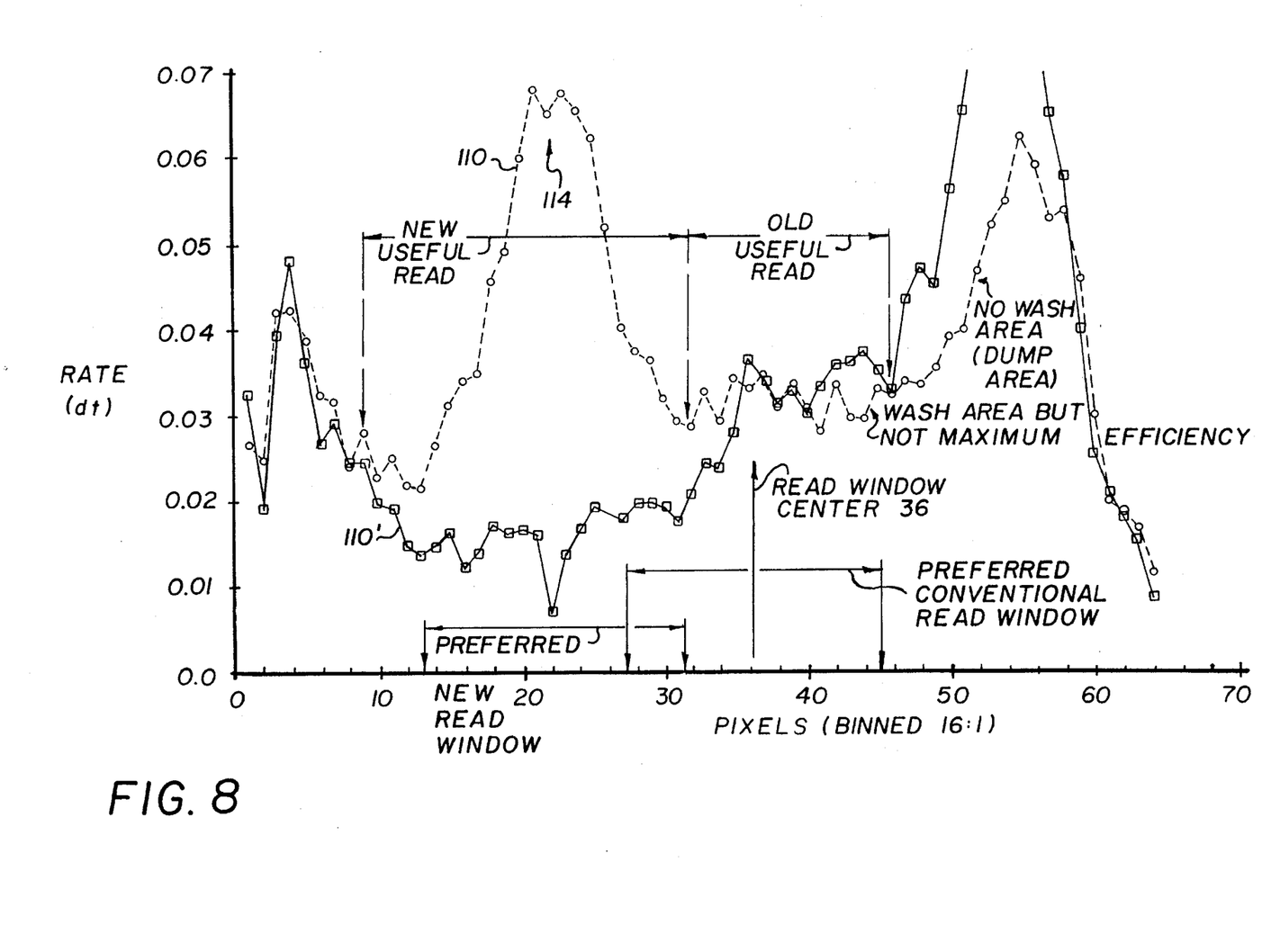
FIG. 8 is a line plot of the center diameter of the mapping of FIGS. 7A and 7B.

FIG. 8 illustrates the drastic variation in rate that occurred in such a test. That is, line plot 110 is the rate detected by scanning from left to right along line of FIG. 7A. The dark spot left of center in FIG. 7A is of course peak 114, FIG. 8. If the area of actual read can always be maintained relative to the slide test elements, then even if centered at pixel 36 as shown for "preferred conventional read window," part of the dark spot ends up being detected. Stated in other words, the "old useful read" window becomes only the valley portion so labeled between pixel 32 and pixel 45, a distance less than actual read diameter of 18 pixels. This is clearly unsatisfactory.

Example 2

Wash According to the Invention

Example 1 was repeated, except the wash was applied over a period of 30 sec, following the dispense curve 50 of FIG. 6. Thus, until 18 sec of wash occurred, it was in the form of separate drops, 0.5 μL in diameter, applied at the rate noted. Starting at 18 sec, the rate was again increased and because the fluid up take crossed the dispense rate at 18 sec, the meniscus in the test element built up rapidly to force the dispensed liquid to appear as a continuous stream as depicted at time $t_{i+5}$ in FIG. 2B.

Figure 7B:
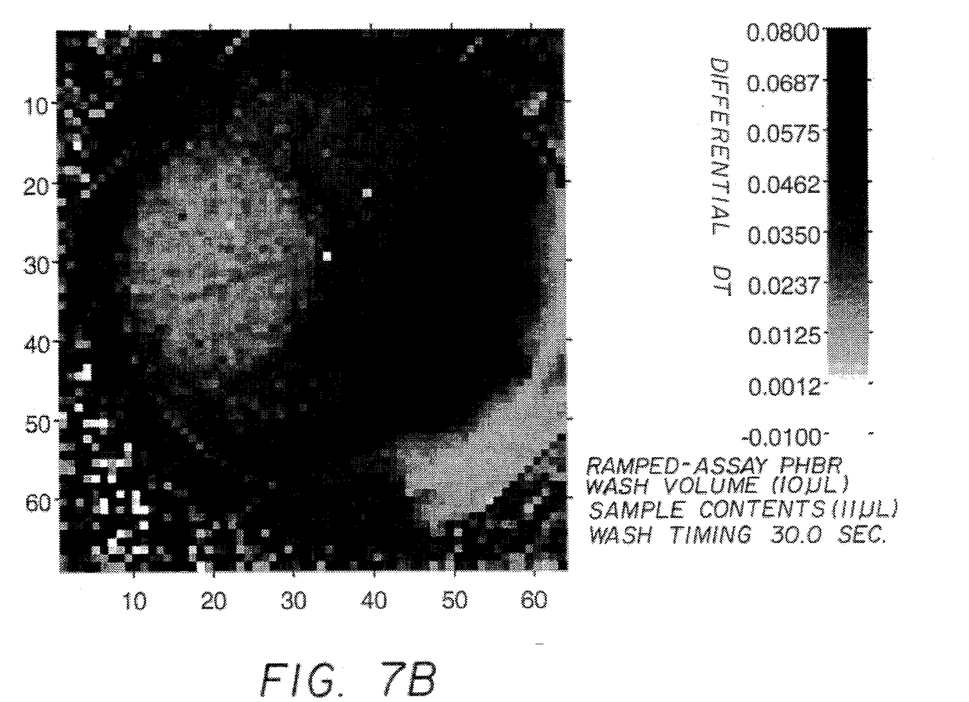

The rate mapping that resulted is shown in FIG. 7B. The dark spot 3.5 mm left of center is conspicuously absent, even though that was the location of the dispense tip. The actual read window of the image of FIG. 7B overlaps only a trace of slightly increased rate.

When the mapping of FIG. 7B is traced along a center line thereof, the result is line plot 110', FIG. 8. Using the same diameter read window of 18 pixels as for line plot 110, the center for the "preferred new read window" becomes pixel 22. Importantly, a much wider latitude is possible ("new useful read") beyond just pixel 13 to pixel 31, since even pixels 9–12 and pixel 32 is useful, unlike the boundaries of the "preferred conventional read window." Even more importantly, the average rate reading of the window for plot 110' (0.02841) is reduced far below the average rate reading of the window for plot 110 (0.03145), meaning that the unwashed free label is less using the wash procedure of Example 2, than it was for the procedure of Example 1.

Finally, this invention has the further advantage that it facilitates the use of a dual wash, that is, washing twice the same test element, if such should be desired. That is, regardless of the composition of such dual washes, the invention by reason of its more complete washing using the minimal volume necessary, makes dual washing more feasible than would be the case where excessive volumes are needed for each wash to be sure that the center under the wash deposition is adequately washed.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In a method of separating bound labeled immunoreactant used to detect a target analyte from free labeled immunoreactant used to detect said analyte in an immunoassay conducted on a test element containing dried reagents prior to contact with a sample liquid and having a determinable rate of liquid uptake, the method comprising the step of depositing a wash liquid onto a portion of said test element having a surface and containing both said bound and said free labeled immunoreactants so as to separate said bound from said free labeled immunoreactants;

the improvement wherein the depositing step comprises the steps of a) initially depositing the wash liquid a drop at a time at a rate that is less than the rate of uptake of each drop by said portion of said test element, so that a minimal remaining meniscus of the wash liquid remains at the surface of said portion when the next of the wash liquid is applied, said drops having a volume no larger than about 3 μL; and b), after a plural number of drops are applied as per step a), applying the wash liquid at a rate that exceeds the rate of uptake of liquid as it currently exists in the test element portion being contacted by the wash liquid in step b) only, more than said minimal remaining meniscus of the wash liquid forms and remains during the washing of said surface, to effect the separation of said bound from said free labeled immunoreactants, wherein the total wash volume is deposited within a time not exceeding about 60 seconds.

2. The method as defined in claim 1, wherein said drops of said step a) have a volume producing a contact diameter with said test element that is less than the contact diameter that would be produced if the depositing were in the form of a continuous stream.

3. The method as defined in claim 1, wherein said step b) comprises applying the wash liquid at a rate that causes said remaining meniscus size to increase over time until all the wash liquid is deposited.

4. The method as defined in claim 1, wherein said step b) comprises increasing the rate of application of the wash liquid above the rate used in said step a) so as to minimize the time required for said washing, until all the wash liquid is deposited.

5. The method as defined in claim 1, wherein said step b) applies the wash liquid at the same depositing rate used in said step a), but the uptake rate of said test element portion decreases over time between steps a) and b) to a value that is less than the rate of application of step b).

6. The method as defined in claim 1, wherein said drop volume is no larger than about 2 μL.

7. In a method of separating bound labeled immunoreactant used to detect a target analyte from free labeled immunoreactant used to detect said analyte in an immunoassay conducted on a test element containing reagents, the method comprising the step of depositing a wash liquid onto a portion of said test element containing both said bound and said free labeled immunoreactants; the improvement wherein the depositing step comprises the steps of a) repeatedly washing the portion of said test element at an approximate center of the contact of said deposited wash liquid by repeatedly passing a contact meniscus of the deposited wash liquid through said portion, and b) thereafter expanding the contact meniscus out beyond said portion of the test element being washed, until all the wash liquid is deposited within a total depositing time no greater than about 60 seconds.

8. The method as defined in claim 7, wherein the volume of said repeated, deposited wash liquid producing said contact meniscus, is no larger than about 2 μL.

* * * * *